United States Patent
Haushalter et al.

(10) Patent No.: US 10,351,881 B2
(45) Date of Patent: Jul. 16, 2019

(54) HOST CELLS AND METHODS FOR PRODUCING DIACID COMPOUNDS

(71) Applicant: The Regents of the University of California, Oakland, CA (US)

(72) Inventors: Robert W. Haushalter, Emeryville, CA (US); Jay D. Keasling, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 11 days.

(21) Appl. No.: 15/067,121

(22) Filed: Mar. 10, 2016

(65) Prior Publication Data

US 2017/0016034 A1    Jan. 19, 2017

Related U.S. Application Data

(60) Provisional application No. 62/130,971, filed on Mar. 10, 2015.

(51) Int. Cl.
*C12P 7/44* (2006.01)
*C12P 17/08* (2006.01)
*C12N 9/16* (2006.01)
*C12N 9/10* (2006.01)

(52) U.S. Cl.
CPC .............. *C12P 7/44* (2013.01); *C12N 9/1007* (2013.01); *C12N 9/16* (2013.01); *C12P 17/08* (2013.01); *C12Y 201/01197* (2013.01); *C12Y 301/02* (2013.01)

(58) Field of Classification Search
None
See application file for complete search history.

(56) References Cited

U.S. PATENT DOCUMENTS

2011/0118433 A1   5/2011   Poetter et al.
2013/0267012 A1   10/2013  Steen et al.

OTHER PUBLICATIONS

Lin, S. & Cronan, J.E., "The BioC O-Methyltransferase Catalyzes Methyl Esterification of Malonyl-Acyl Carrier Protein, an Essential Step in Biotin Synthesis", Oct. 2012, The Journal of Biological Chemistry vol. 287, No. 44, pp. 37010-37020.*
Liu et al., "Production of extracellular fatty acid using engineered *Escherichia coli*", Microbial Cell Factories 2012, 11:41.*
White et al., "The Structural Biology of Type II Fatty Acid Biosynthesis", Annu. Rev. Biochem. 2005. 74:791-831 doi: 10.1146/annurev.biochem.74.082803.133524.*
Swift, K.A.D. (ed.), Current Topics in Flavours and Fragrances—Towards a New Millennium of Discovery, Springer Science+ Business Media, B.V., pp. 81-85 (1999).

* cited by examiner

*Primary Examiner* — Suzanne M Noakes
(74) *Attorney, Agent, or Firm* — Robin C. Chiang; Lawrence Berkeley Nation Laboratory

(57) ABSTRACT

The present invention provides for a genetically modified host cell and related methods and materials for the biocatalytic production of an α,ω-dicarboxylic acids (DCAs) and/or mono-methyl ester derivatives of dicarboxylic acids (DCAMMEs).

16 Claims, 6 Drawing Sheets

Specification includes a Sequence Listing.

PRIOR ART

Figure 9

HOST CELLS AND METHODS FOR PRODUCING DIACID COMPOUNDS

RELATED PATENT APPLICATIONS

The application claims priority to U.S. Provisional Patent Application Ser. No. 62/130,971, filed Mar. 10, 2015; which is incorporated herein by reference.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of production of dicarboxylic acids and ester derivatives of dicarboxylic acids.

BACKGROUND OF THE INVENTION

Dicarboxylic acids and corresponding mono-methyl esters have numerous industrial and medicinal applications, including, but not limited to, production of nylons and other polymers, constituents of cosmetics, fragrances, and acne medications.

People currently use a variety of chemical processes to produce dicarboxylic acids. Oxidation of cyclic ketones, such as cyclohexanone, or unsaturated fatty acids, such as oleic acid, is commonly used for the synthesis of dicarboxylic acids. Currently the most widely used method to produce dicarboxylic acids currently is the bioconversion of the corresponding alkane with *Candida tropicalis*. This yeast expresses oxidase enzyme complexes that oxidize the termini of alkanes to the corresponding carboxylic acid. U.S. Patent Application Publication No. 2011/0118433 discloses using genetically engineered *Candida tropicalis* cells to produce ω-hydroxycarboxylic acids and ω-hydroxycarboxylic acid esters. This method requires feeding of purified alkanes or fatty acids to the cells, using cytochrome P450s, and is limited to *Candida tropicalis* cells (see FIGS. 1 and 6). U.S. Patent Application Publication No. 2013/0267012 discloses a method of producing one or more fatty acid derived dicarboxylic acids in a genetically modified host cell which does not naturally produce the one or more derived fatty acid derived dicarboxylic acids.

Dicarboxylic acids are precursors to materials like polyesters and nylons, as well as high-value fragrance molecules like ethylene brassylate (see FIG. 2).

SUMMARY OF THE INVENTION

This present invention provides for a genetically modified host cell and related methods and materials for the biocatalytic production of an α,ω-dicarboxylic acids (DCAs) and/or mono-methyl ester derivatives of dicarboxylic acids (DCAMMEs). The DCAs and DCAMMEs can be used in the production of renewable chemicals for use in applications, including making polyesters, resins, polyamides, nylon, fuel additives and fuels, lubricants, paints, varnishes, engineering plastics and the like.

The genetically modified host cell comprises (a) a first enzyme having a first enzymatic activity that catalyzes a methyl transfer to an acyl-ACP species with a free carboxylate group distal to the thioester bond to form a first intermediate compound, (b) optionally enzymes having enzymatic activities that elongate the first intermediate molecule to form a second intermediate compound, and (c) optionally a second enzyme activity that catalyzes a release of the first or second intermediate molecule from the ACP through thioester hydrolysis to form a DCA or DCAMME. The DCAMME can also further undergo hydrolysis to form a DCA.

The present invention provides for a recombinant or genetically modified host cell, such as a recombinant or genetically modified of *E. coli*, that is capable of producing one or more DCAs and/or DCAMMEs from a carbon source, such as glucose.

In some embodiments, the genetically modified host cells are capable, when cultured, to produce a dicarboxylic acid with a carbon backbone with an odd-number of carbon atoms. In some embodiments, the genetically modified host cell extends a three-carbon precursor, such as malonyl-ACP, two-carbons at a time to yield a DCA comprising a main carbon chain with an odd number of carbon atoms. FIG. 5 shows a method for producing a DCA with an odd-number of carbons atoms in the main carbon chain from a malonyl-ACP.

The present invention provides for a method for producing dicarboxylic acids (DCAs) and mono-methyl ester derivatives of dicarboxylic acids (DCAMMEs) in microbes by altering the expression of several genes. Dicarboxylic acids are industrially and medicinally relevant compounds. In some embodiments, the method comprises: (a) providing the genetically modified host cell of the present invention, (b) culturing or growing the genetically modified host cell such that a DCA and/or a DCAMME is produced, (c) optionally separating the DCA and/or the DCAMME from the genetically modified host cell, and (d) optionally polymerizing the DCA and/or the DCAMME into a polyester or polyamide polymer.

In some embodiments, the polymerizing step comprises reacting the DCA with a diamine to produce a nylon. A suitable diamine is an alkane diamine, such as hexane-1,6-diamine. In some embodiments, the polymerizing step comprises reacting the DCA with a dialcohol to produce a polyester. A suitable dialcohol is an alkane diol, such as ethylene glycol, propane diol, or butanediol. (See FIG. 7.) In some embodiments, the method further comprises converting the DCA into a macrocyclic musk using a scheme as described in FIG. 8. In some embodiments, the method further comprises cyclizing of the polyester into a macrocyclic musk, such as described in Scheme 1 of FIG. 8.

The DCA provides for the production of "green" nylon, such as that used in Mohawk carpet fibers. Besides nylon production, the ability to manipulate the side chains of the DCA provides for the production of novel polymer precursors that would lead to polymers with a variety of properties. These products may also serve as adhesive, lubricants or precursors for pharmaceuticals or other more complicated compounds.

The present invention provides for a composition comprising a DCA and/or a DCAMME isolated from a host cell from which the DCA and/or the DCAMME is produced, and trace residues and/or contaminants of the host cell. Such trace residues and/or contaminants include cellular material produced by the lysis of the host cell.

BRIEF DESCRIPTION OF THE DRAWINGS

The foregoing aspects and others will be readily appreciated by the skilled artisan from the following description of illustrative embodiments when read in conjunction with the accompanying drawings.

FIG. 9. Clustal W alignment of *B. cereus* ATCC10987 (top line) and *E. coli* MG1655 BioC (second line) together with the BioCs of several diverse bacteria. The diverse bacteria (followed by their GenBank™ accession numbers in parentheses) are *Kurthia*, *Kurthia* sp. 538-KA26 (BAB39463); *Cl thermo*, *Clostridium thermocellum* (ABN51266); *Ch tepidum*, *C. tepidum* (NP_660955); *Serratia* sp., *Serratia marcescens* (P36571); and *E. herbicola*, *Erwinia herbicola* (O06898) (SEQ ID NOs: 1-7, respectively). The accession numbers of the *B. cereus* and *E. coli* proteins are NP_980478 and NP_415298, respectively.

DETAILED DESCRIPTION OF THE INVENTION

Figure 1:
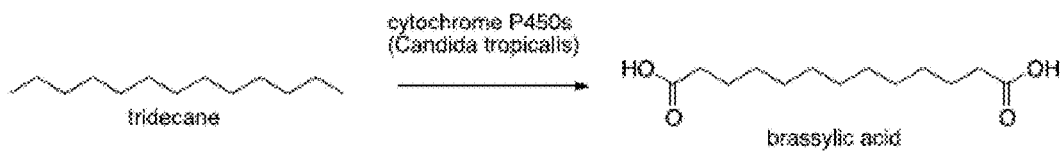
FIG. 1. A current method for producing DCA.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

In some embodiments, the DCAMME has the chemical formula:

(I)

In some embodiments, the DCA has the chemical formula:

(II)

In some embodiments, the DCA has the chemical formula:

(IIa)

In some embodiments, the DCA is chemically polymerized into a polyester or polyamide (nylon) polymer having the chemical formula:

(III)

or (IV)

respectively.

In some embodiments, for chemical formulae (I), (II), (III), or (IV), n is an integer from 1 to 30. In some embodiments, n is an integer from 1 to 20. In some embodiments, n is an integer from 1 to 10. In some embodiments, n is the integer 1, 2, 3, 4, or 5. In some embodiments, n is an odd integer, such as any odd integer from the ranges described above. In some embodiments, n is an even integer, such as even odd integer from the ranges described above.

In some embodiments, the DCA is an α,ω-dicarboxylic acid having a carbon length ranging from C3 to C25, with an odd number of carbons. Such DCAs include, but are not limited to, a C3 diacid, C5 diacid, C7 diacid, C9 diacid, C11 diacid, C13 diacid, C15 diacid, C17 diacid, C19 diacid, C21 diacid, C23 diacid, and C25 diacid. In some embodiments, the DCA is an α,ω-dicarboxylic acid having a carbon length ranging from C4 to C26, with an even number of carbons. Such DCAs include, but are not limited to, a C4 diacid, C6 diacid, C8 diacid, C10 diacid, C12 diacid, C14 diacid, C16 diacid, C18 diacid, C20 diacid, C22 diacid, C24 diacid, and C26 diacid.

In some embodiments, the genetically modified host cell is transformed with a first nucleic acid construct encoding the first enzyme. In some embodiments, the first nucleic acid further encodes, or the genetically modified host cell is transformed with a first nucleic acid construct encoding, the enzymes having enzymatic activities that elongate the first intermediate molecule to form a second intermediate compound. In some embodiments, the first nucleic acid or second nucleic acid further encodes, or the genetically modified host cell is transformed with a third nucleic acid construct encoding the second enzyme. In some embodiments, the genetically modified host cell is of a species wherein the genome of the wild-type host cell encodes the first enzyme and/or the enzymes having enzymatic activities that elongate the first intermediate molecule to form a second intermediate compound.

In some embodiments, the genetically modified host cell is of a species wherein the genome of the wild-type host cell does not have any one, any two, or all of the first enzyme, the enzymes having enzymatic activities that elongate the first intermediate molecule to form a second intermediate compound, and the second enzyme. In some embodiments, the genetically modified host cell is of a species wherein the genome of the wild-type host cell encodes any one, any two, or all of the first enzyme, the enzymes having enzymatic activities that elongate the first intermediate molecule to form a second intermediate compound, and the second enzyme, and the genetically modified host cell is capable of overexpressing the one, two, or all of the first enzyme, the enzymes having enzymatic activities that elongate the first intermediate molecule to form a second intermediate compound, and the second enzyme compared to the expression of each corresponding enzyme in the wild-type host cell.

In some embodiments, the first enzyme is a BioC, or a polypeptide having an amino acid sequence that has at least 70% amino acid sequence identity, or at least 75%, 80%, 85%, 90%, 95%, or 99% or greater amino acid sequence identity, to any one of SEQ ID NO:1-9. In some embodiments, the polypeptide comprises one or more, or all, of conserved residues indicated by an asterisk and/or boxed for all seven BioH shown in FIG. 9.

In some embodiments, the acyl-ACP species is malonyl-ACP and the first intermediate molecule is malonyl-ACP methyl ester. In some embodiments, the acyl-ACP species is succinyl-ACP and the first intermediate molecule is succinyl-ACP methyl ester.

In some embodiments, the BioC is *Bacillus cereus* BioC having the following amino acid sequence:

```
                                             (SEQ ID NO: 8)
         10         20         30         40
MINKTLLQKR FNGAAVSYDR YANVQKKMAH SLLSILKERY 50         60         70         80
SETASIRILE LGCGTGYVTE QLSKLFPKSH ITAVDFAESM 90        100        110        120
IAIAQTRQNV KNVTFHCEDI ERLRLEESYD VIISNATFQW 130        140        150        160
LNNLQQVLRN LFQHLSIDGI LLFSTFGHET FQELHASFQR 170        180        190        200
AKEERNIKNE TSIGQRFYSK DQLLHICKIE TGDVHVSETC 210        220        230        240
YIESFTEVKE FLHSIRKVGA TNSNEGSYCQ SPSLFRAMLR 250        260
IYERDFTGNE GIMATYHALF IHITKEGKR
```

In some embodiments, the BioC is *Pseudomonas putida* BioC having the following amino acid sequence:

```
                                             (SEQ ID NO: 9)
         10         20         30         40
MTDLSRPTLP GALPDKRQVA ASFSRAAASY DSVAALQRAV 50         60         70         80
GLSLLEQLPA GLQPSHWLDL GSGTGHFSRM LAERFAQAGG 90        100        110        120
VAVDIAEGML LHARHVKGGA QYHVVGDAER LPLRDASVDL 130        140        150        160
VFSSLAVQWC DQFASVLAEA QRVLRPGGVL AFSSLCVGTL 170        180        190        200
DELRASWQAV DGLVHVNRFR RFEDYQRLCA ASGFEQLELE 210        220        230        240
RCPHVLHYPD VRSLTHELKA LGAHNLNPGR PSGLTGRARM 250        260        270
QGLLQAYEAF RQPAGLPATY QVVYGVLRKP LA
```

Figure 9:
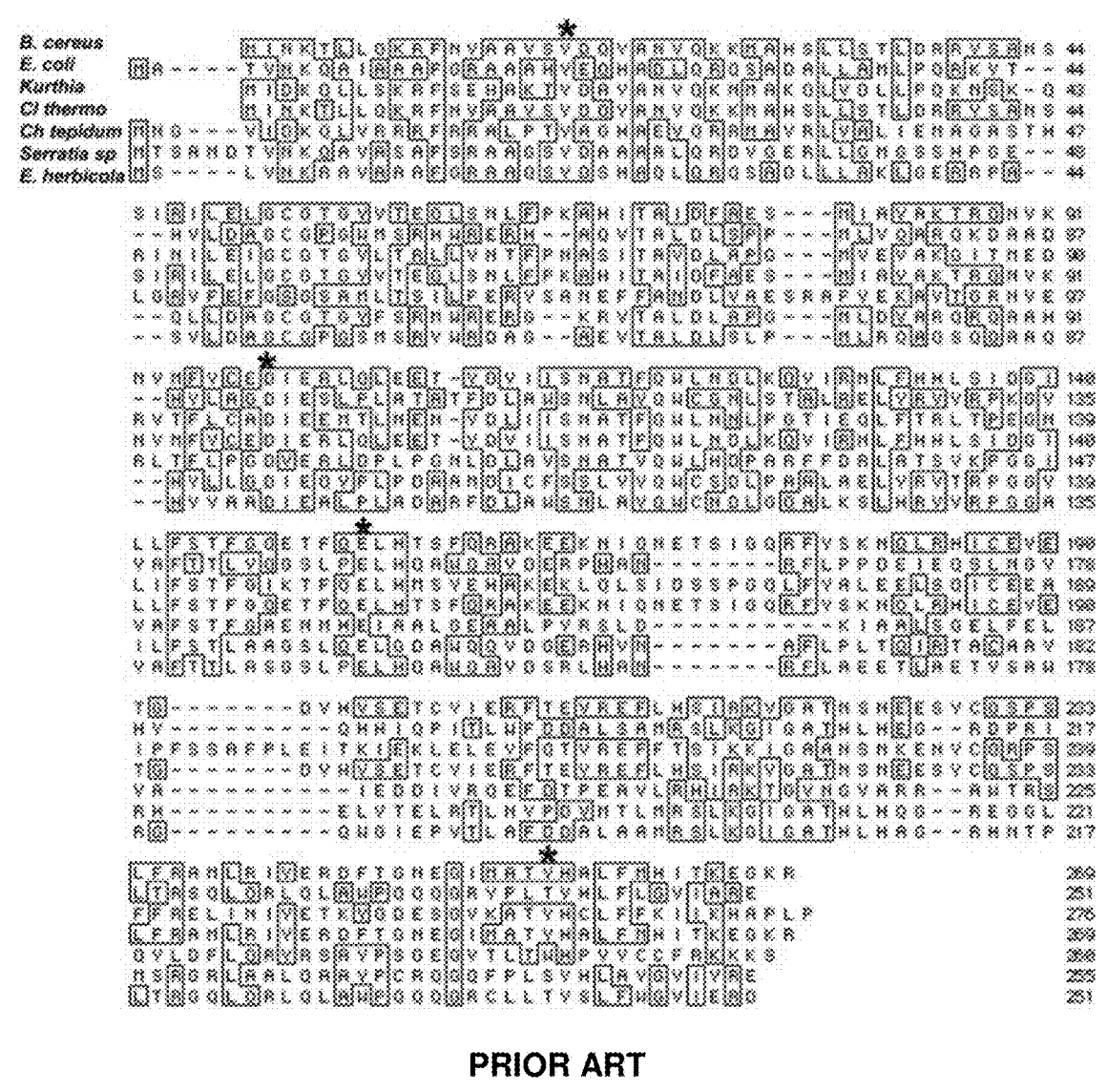

In some embodiments, the BioC has the amino acid sequence show in FIG. 9.

In some embodiments, the enzymes having enzymatic activities that elongate the first intermediate molecule to form a second intermediate compound is a FAS. The FAS can be of the Type I, Type II, and Type III fatty acid systems. Type I and Type III fatty acid systems often contain multiple enzymatic activities on a single polypeptide chain and are referred to as elongases for the Type III system. Generally, Type I and Type III systems generate specific chain length acyl-CoA molecules, which are normally transferred directly into the production of membrane lipids (phospholipids, glycerolipids, etc.) but can be hydrolyzed by a thioesterase to release the free fatty acid in engineered systems. Type II fatty acid systems are composed of single polypeptides that individually encode the multiple enzymatic activities required for fatty acid biosynthesis to generate a range of fatty acyl-ACPs that are normally transferred directly into the production of membrane lipids, but can be hydrolyzed by a thioesterase that recognizes specific chain length fatty acids.

In some embodiments, the FAS is a FAS2 or Type II fatty acid synthase, such as *Aspergillus parasiticus* FAS2 (AY371490) or *S. cerevisiae* FAS2 (α-subunit of fatty acid synthase; NP_015093.1).

In some embodiments, the second enzyme is a cytosolic thioesterase or 'TesA. The 'TesA can be cloned using the methods taught in U.S. Patent Application Publication No. 2013/0267012, which is hereby incorporated by reference.

In some embodiments, the genetically modified host cell is reduced, or lacks, the enzymatic activity of BioH. In some embodiments, the wild-type genome of the genetically modified host cell encodes an enzyme having the enzymatic activity of BioH, such as a bioH gene. In some embodiments, the genetically modified host cell is genetically modified to reduce, or lack, the enzymatic activity of BioH, or expression of the bioH gene. In some embodiments, the genetically modified host cell is genetically modified to reduce expression of or knock-out the naturally occurring bioH gene. In some embodiments, the native promoter of the bioH gene is deleted in order to reduce expression of the bioH open reading frame. In some embodiments, the genetically modified host cell is heterologous to any one of the first enzyme, the enzymes having enzymatic activities that elongate the first intermediate molecule to form a second intermediate compound, and/or second enzymes. In some embodiments, the genetically modified host cell naturally lacks a native BioH.

In some embodiments, the genetically modified host cell overexpresses BioC and 'TesA in a ΔbioH genetic background.

Fatty acid synthase enzymes are able to extend pimeloyl-ACP methyl ester further, and that 'TesA is able to efficiently catalyze hydrolysis of non-native long chain DCAMME acyl groups from ACP.

The genetically modified host cell can be any microbe capable of production of fatty acid-derived chemicals in accordance with the methods of the invention. In various embodiments, the microbes have characteristics that allow them to produce higher levels of product. For example, in one embodiment, the genetically modified host cell provided by the invention lacks or has reduced expression levels of, or has been modified for decreased activity of, enzymes catalyzing the degradation of specific chain length fatty acids. These enzyme activities include CoA-ligases (for example, and without limitation, FadD (*E. coli*), FAA1, FAA2, FAA3, FAA4 (*S. cerevisiae*), etc. as provided later and enzymes necessary for beta oxidation of fatty acids (for example, and without limitation, POX1, POX2, IDP3, TES1, FOX3 (*S. cerevisiae*), etc as provided later). In some embodiments, diols are produced from fatty acids. In these embodiments, enzymes necessary for beta oxidation will be reduced, but CoA-ligases may be retained.

Because malonyl-CoA is a possible precursor to fatty acid synthesis, it is advantageous to upregulate malonyl-CoA biosynthesis. In various embodiments, the genetically modified host cell is engineered for increased expression of enzymes catalyzing production of malonyl-CoA. For example, and without limitation, increasing the expression level of acyl-CoA carboxylase (gene ACC1 (FAS3) in *S. cerevisiae* is included herein for reference).

In some embodiments, the genetically modified host cell exhibits improved production of fatty acids and the corresponding diacid products. In some embodiments, the genetically modified host cell has reduced expression of genes and/or the corresponding enzyme products associated with fatty acid, α,ω-dicarboxylic acid, and related product, beta-oxidation, and have increased expression of genes and/or their corresponding enzyme products associated with α,ω-dicarboxylic acid and related product transporters. In this manner, the genetically modified host cell is deficient in its ability to degrade the final fatty acid or α,ω-dicarboxylic acid product and/or secretes product into the fermentation broth. Furthermore, in some embodiments, the genetically modified host cell is engineered for increased expression of genes and/or their corresponding enzyme products associated with biosynthesis of malonyl-CoA.

In some embodiments, the genetically modified host cell comprises (a) a BioC having a enzymatic activity that catalyzes a methyl transfer to an acyl-ACP species with a free carboxylate group distal to the thioester bond to form a first intermediate compound, (b) optionally FAS having enzymatic activities that elongates the first intermediate molecule to form a second intermediate compound, and (c) optionally a 'tesA that catalyzes a release of the second intermediate molecule from the ACP through thioester hydrolysis to form a DCA or DCAMME. The DCAMME can also further undergo hydrolysis to form a DCA.

In some embodiments, the host organism is yeast. Yeast host cells suitable for practice of the methods of the invention include, but are not limited to, *Yarrowia, Candida, Bebaromyces, Saccharomyces, Schizosaccharomyces* and *Pichia*, including engineered strains provided by the invention. In one embodiment, *Saccharomyces cerevisae* is the host cell. In one embodiment, the yeast host cell is a species of *Candida*, including but not limited to *C. tropicalis, C. maltosa, C. apicola, C. paratropicalis, C. albicans, C. cloacae, C. guillermondii, C. intermedia, C. lipolytica, C. panapsilosis* and *C. zeylenoides*. In one embodiment, *Candida tropicalis* is the host cell.

In some embodiments the host is bacteria. Bacterial host cells suitable for practice of the methods of the invention include, but are not limited to, *Escherichia* and *Bacillus*, including engineered strains provided by the invention. In one embodiment, the bacterial host cell is a species of *Bacillus*, including but not limited to *B. subtilis, B. brevis, B. megaterium, B. aminovorans*, and *B. fusiformis*. In one embodiment, *B. subtilis* is the host organism.

One can modify the expression of a gene encoding any of the enzymes taught herein by a variety of methods in accordance with the methods of the invention. Those skilled in the art would recognize that increasing gene copy number, ribosome binding site strength, promoter strength, and various transcriptional regulators can be employed to alter an enzyme expression level. The present invention provides a method of producing a DCA and/or a DCAMME in a genetically modified host cell that is modified by the increased expression of one or more genes taught herein, and optionally one or more genes involved in the production of the acyl-ACP, such as malonyl-ACP or succinyl-ACP. This may include any genes involved in the production of fatty acid compounds by the host cell. In some embodiments, the genetically modified host cell further comprises modification of such genes. Such genes include, without limitation, those that encode the following enzymatic activities: acetyl CoA carboxylase, ketosynthase, ketoreductase, dehydratase, enoyl reductase, cytosolic thioesterase, and acyl-carrier protein. Illustrative genes that encode these enzymatic functions include acpP, acpS, accA, accB, accC, accD, fabD, fabH, fabG, fabZ, fabA, fabI, fabB, fabF (suitable copies of these genes may be obtained from, and without limitation, *E. coli, Bacillus subtilis*), tesA, tesB (*E. coli*), yneP, ysmA, ykhA, yvaM, ylpC (*B. subtilis*), FAS1, FAS2, FAS3, ELO1, ELO2, ELO3 (*S. cerevisiae*), ELO1, ELO2, ELO3 (*T. brucei, T. cruzi, L. major*), fasA, fasB (*C. glutamicum, B. ammoniagenes, C. ammoniagenes*), FAS1 (*Mycoplasma tuberculosis, Mycoplasma. smegmatis*), and hexA, hexB (*A. flavus, A. parasiticus*). In some embodiments, one increases transcriptional regulation of these genes. Suitable transcriptional regulators include fadR (suitable copies of these genes may be obtained from, and without limitation, *E. coli* or *B. subtilis*) and RAP1, ABF1, REB1, INO2, INO4 (*S. cerevisiae*).

The present invention also provides methods and genetically modified host cells that have been engineered to be capable of secreting or excreting the DCA and/or DCAMME into the media. In some embodiments, genetically modified host cells and methods are provided to make the DCA and/or DCAMME that are secreted or excreted into the media or fermentation broth. In particular embodiments, these genetically modified host cells are further modified by expression of one or more genes encoding proteins involved in the export of DCA and/or DCAMME such that the product is moved from the interior of the cell to the exterior. Such genes include the following: DAL5, DIP5, JEN1 (*S. cerevisiae*), MAE1 (*Schizosaccharomyces pombe*), atoE, citT (*B. subtilis*), dcuB, dcuC (*B. subtilis, A. succinogenes, E. coli*), and various multidrug resistance pumps.

Once in the media or fermentation broth, the DCA and/or DCAMME can be separated and purified in accordance with the invention. In some embodiments, the genetically modified host cells is modified to secrete the DCA and/or DCAMME, and subsequently purified from the broth. In some embodiments, the products are purified through precipitation as calcium salts, or reactive extraction with tertiary amines. In some embodiments, the tertiary amines employed include, and without limitation, tripropylamine, trioctylamine, or tridecylamine. In some embodiments, ion exchange is employed for further purification of the DCA and/or DCAMME.

In other embodiments, the host cells are not modified to secrete the product into the growth medium and the product accumulates in the host cell. In these embodiments, the DCA and/or DCAMME is separated from the host cell in accordance with the invention by centrifugation or settling of the cell material, cell lysis, and subsequent purification of the DCA and/or DCAMME.

In some embodiments, the first, second, and/or third nucleic acid are recombinant DNA vectors.

Pimeloyl-acyl carrier protein, or pimeloyl-ACP, as well as pimeloyl-ACP methyl ester, are intermediates in the biosynthesis of the cofactor biotin. The pimeloyl moiety is produced in three steps: (1) methylation of malonyl-ACP by the methyltransferase BioC to yield malonyl-ACP methyl ester, (2) two iterations of condensation and reduction by the sequential actions of FabB or FabF, FabG, FabZ, and FabI, enzymes collectively referred to as $E.$ $coli$ fatty acid synthase, to yield pimeloyl-ACP methyl ester, and (3) hydrolysis of the terminal methyl ester moeity by the hydrolase BioH. This pimeloyl-ACP intermediate is then converted to biotin through several additional enzymatic steps. The hydrolysis of the terminal methyl ester of pimeloyl-ACP methyl ester by BioH is thought to prevent further extension of the ACP-bound acyl chain by the fatty acid synthase. Thus, if the activity of BioH is removed, the fatty acid synthase is expected to continue extension of the pimeloyl methyl ester group to yield longer (9-17 carbon) dicarboxyl methyl ester ACP-bound compounds.

The pimeloyl or pimeloyl methyl ester moieties, as well as any longer chemical species formed in the absence of BioH, are covalently bound to ACP through a thioester linkage. If the thioester bond is hydrolyzed, it will release free pimelate, pimelate mono-methyl ester, or extension products into solution. ACP-thioesterase enzymes, such as 'TesA, are capable of catalyzing hydrolysis of acyl-ACP thioesters, releasing the bound substrates into solution.

In some embodiments, the method for producing DCAs and DCAMMEs in $E.$ $coli$ comprises: (a) expressing, such as overexpressing, BioC, or any enzyme capable of catalyzing methyl transfer to malonyl-ACP, succinyl-ACP, or any other acyl-ACP species with a free carboxylate group distil to the thioester bond, and (b) expressing, such as overexpressing, 'TesA or any acyl-ACP thioesterase or acyl-CoA thioesterase capable of releasing bound DCAs and DCAMMEs from ACP though thioester hydrolysis. When BioH is not present in the host cell, the production of DCAs and DCAMMEs is increased.

Other commonly used methods for production of DCAs include oxidation of cyclohexanone, oleic acid, or other unsaturated fatty acids. In these processes, the chain length is completely dependent on the structure of the precursor prior to oxidation. The method described in this invention allows for the production of DCAs with a variety of chain lengths from renewable sources, as well as the mono-methyl ester derivatives.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Host Cell Genetically Modified to Produce Brassylic Acid (C13)

Figure 2:
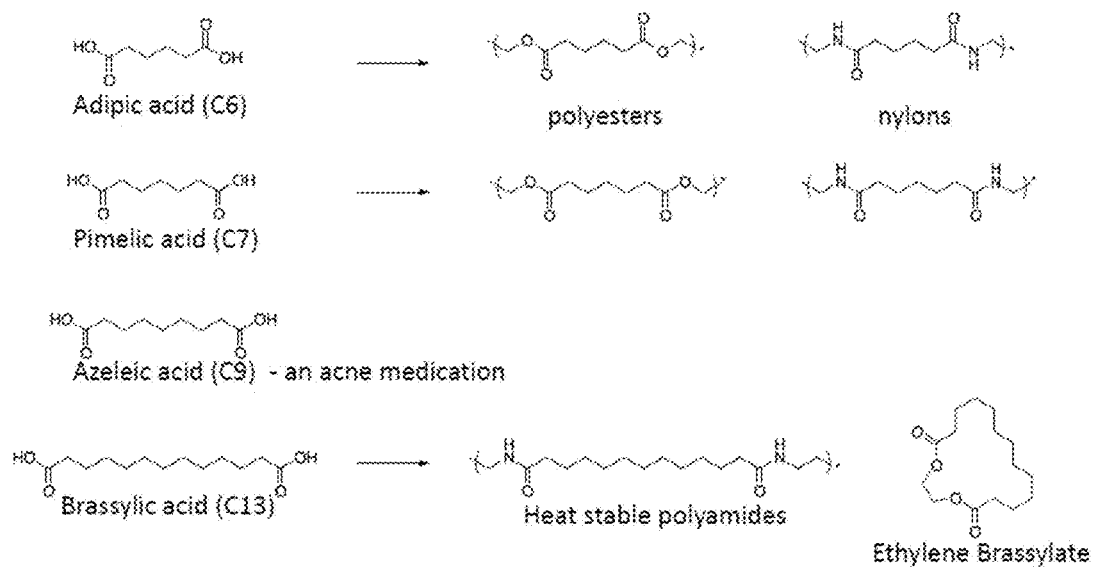
FIG. 2. Current uses for DCA in the chemical industry.
Figure 3:
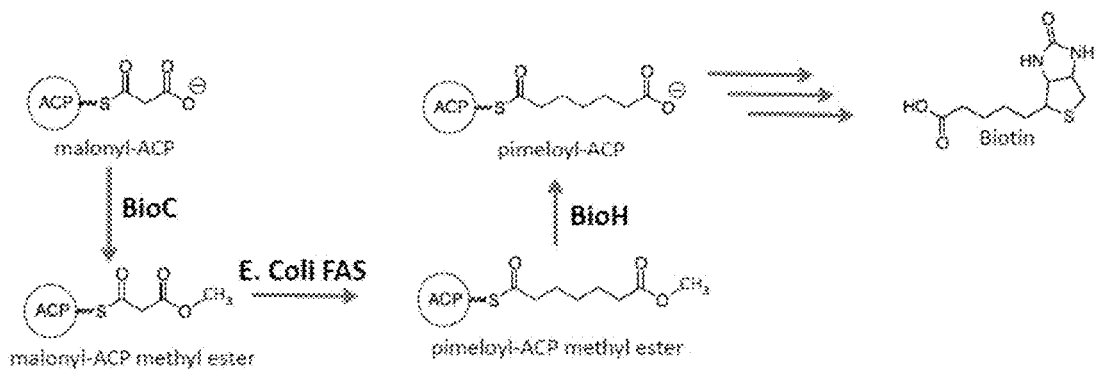
FIG. 3. A method for producing DCAs in *E. coli*. The process begins with malonyl-ACP, an abundant fatty acid precursor in *E. coli*. The carboxyl group is methylated by the enzyme BioC, a S-adenosyl-methionine-dependent methyl transferase (Lin, et al. 2012). The endogenous fatty acid synthase elongates the methylated malonyl group. A hydrolase bioH cleaves the methyl group and the intermediate is processed into biotin.
Figure 4:
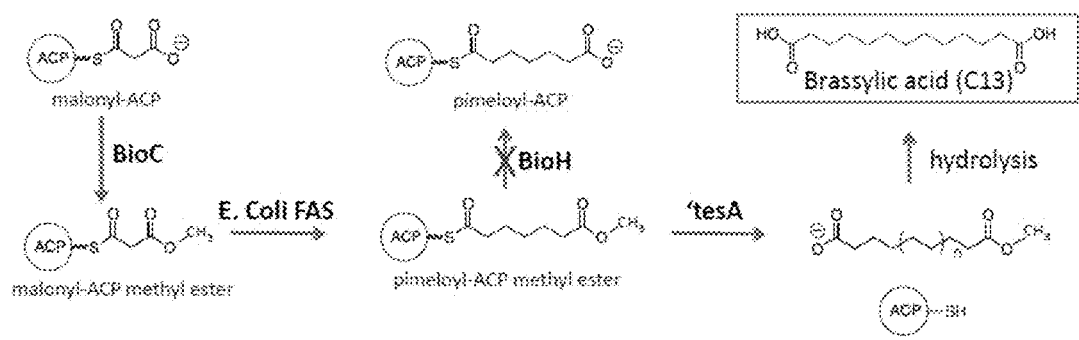
FIG. 4. A method for producing DCAs in *E. coli*.
Figure 5:
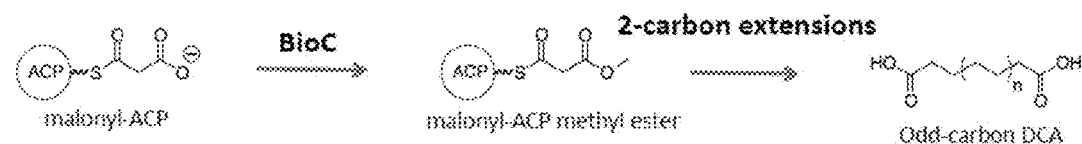
FIG. 5. A method for producing a DCA with an odd-number of carbons atoms in the main carbon chain from a malonyl-ACP.
Figure 6:
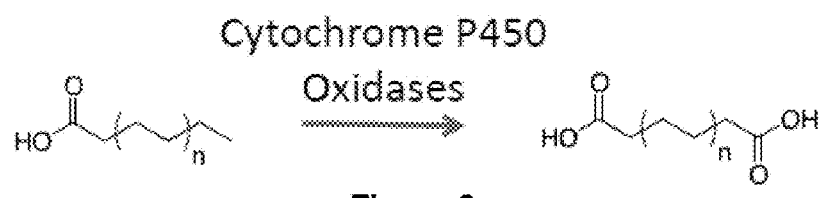
FIG. 6. A method of producing a DCA from a fatty acid precursor.
Figure 7:
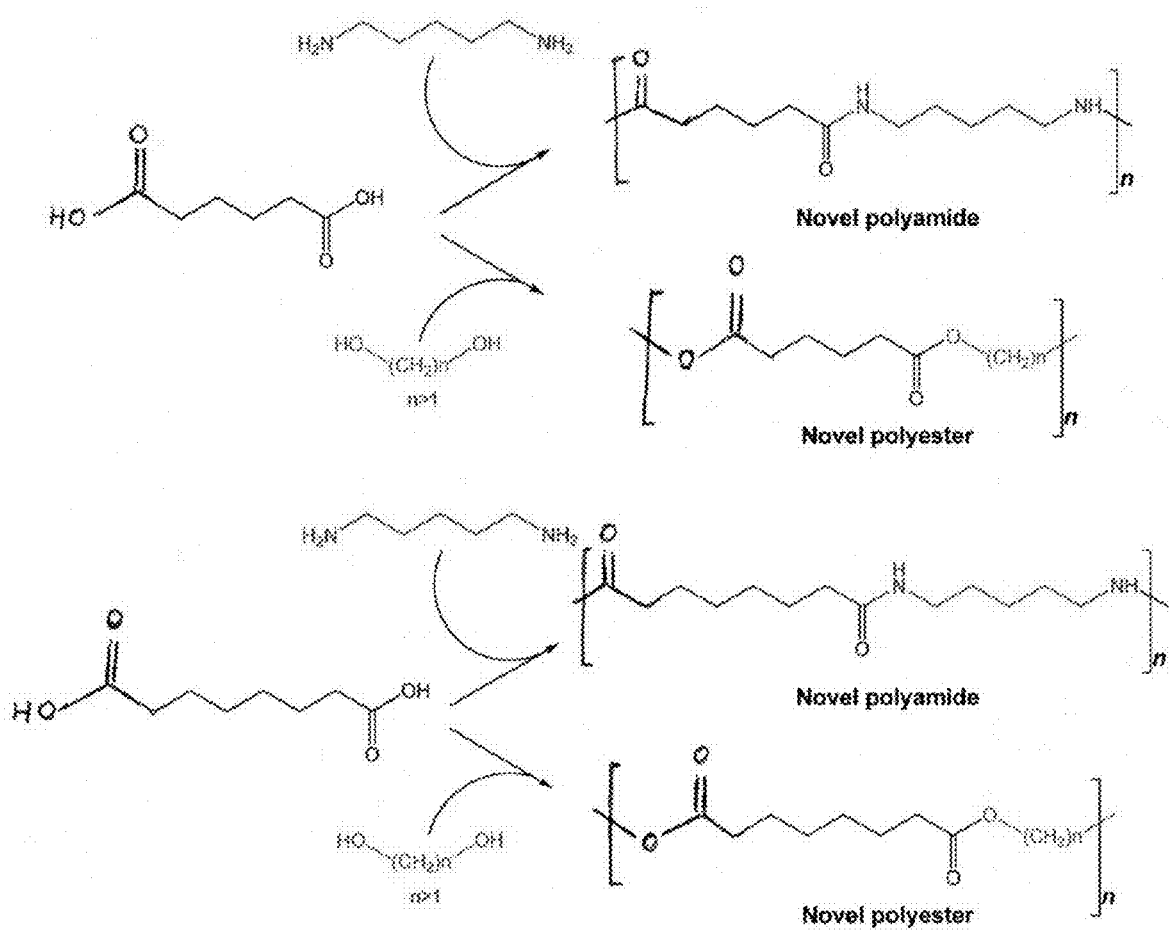
FIG. 7. A scheme for making novel polyamides or novel polyesters using a DCA.
Figure 8:
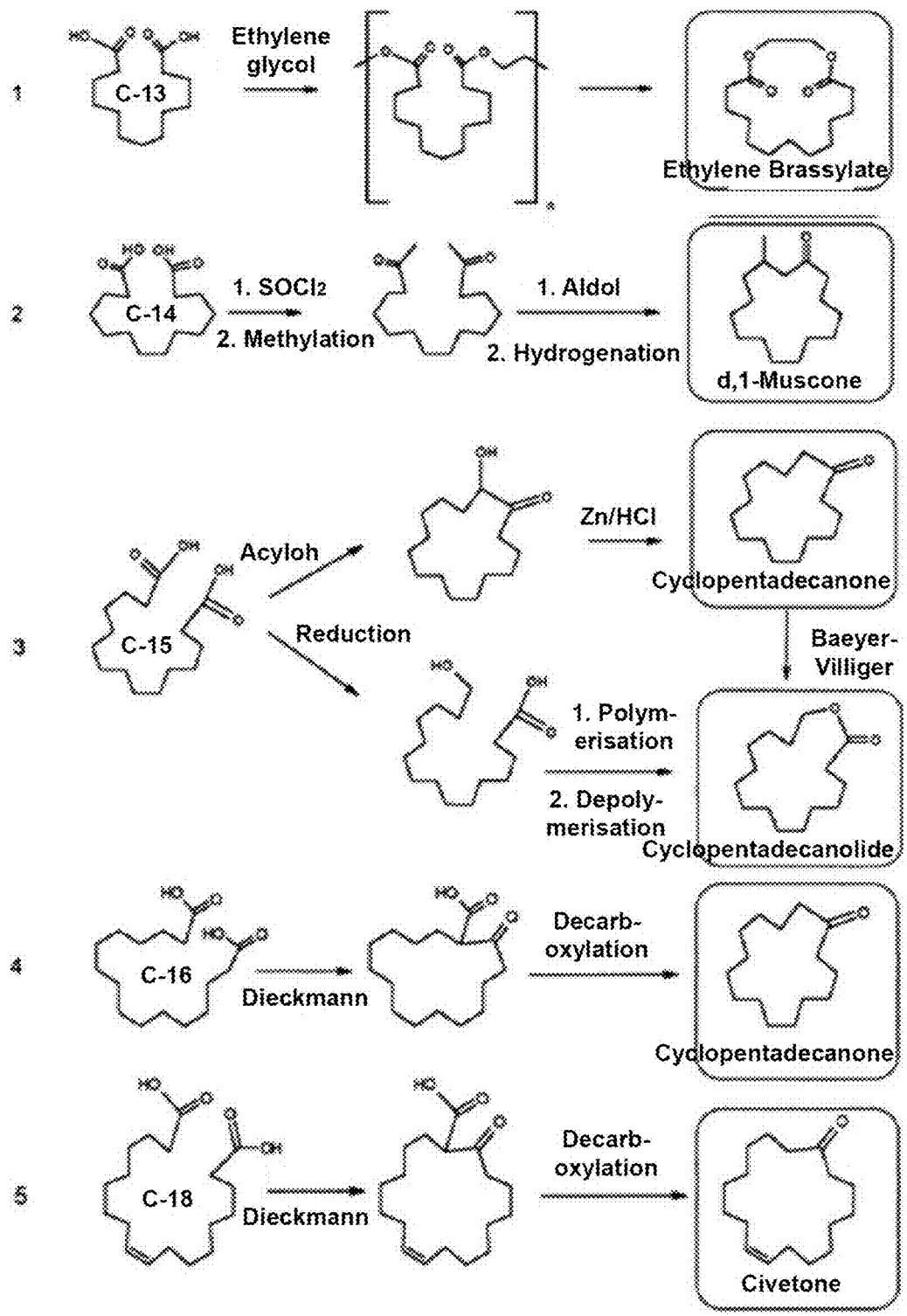
FIG. 8. Schemes for converting a DCA into a macrocyclic musk. The schemes are taught in K.A.D. Swift (ed.), "Current Topics in Flavours and Fragrances—Towards a New Millennium of Discovery", Springer Science+Business Media, B.V., 1999, pp. 81-85.

An $E.$ $coli$ host cell is genetically modified to overexpress BioC and 'TesA in a ΔbioH genetic background (see FIG. 4). The host cell when cultured produces mostly brassylic acid (C13), and trace amounts of C11 diacid and C15 diacid. When compared to results obtained from a control $E.$ $coli$ host cell that is genetically modified to overexpress BioC and 'TesA but in a bioH$^+$ genetic background, the $E.$ $coli$ host cell which overexpresses BioC and 'TesA in a ΔbioH genetic background produces more brassylic acid (C13) than the control host cell. The brassylic acid can be further cyclized into ethylene brassylate (or Musk-T) (see FIG. 2).

Example 2

Method for Production of C13 and C15 Dicarboxylic Acids

Materials and Methods:
Plasmid Construction

Open reading frames encoding BioC from $Bacillus$ $cereus,$ $Pseudomonas$ $putida,$ and $kurthia$ sp. 538-KA26 species are ordered as gblocks from IDT. The sequence for $B.$ $cereus$ bioC is codon optimized, the others are ordered as the wild type DNA sequence. The constructs are PCR amplified and assembled into biobrick expression plasmid pBbE5C or pBbE7C using Gibson cloning.
Strain Construction Strain JBEI-3111 ($E.$ $coli$ MG1655 ΔfadE) has been described previously. The bioH gene is deleted from this strain using P1 phage lysogenization using Keio strain JW3375 as the donor strain, yielding strain JBEI-7954 ($E.$ $coli$ MG1655 ΔfadE ΔbioH).

Strains JBEI-3111 and JBEI-7954 are co-transformed with one of either pBbB5K-'tesA and pBbE5C-bcBioC ($B.$ $cereus$), pBbE5C-pBioC ($P.$ $putida$), or pBbE5C-kBioC ($kurthia$ sp.) to yield production strains.
Cell Culture Production strains are adapted into M9 minimal media (supplemented with 1 mg/L biotin) and expression of 'tesA and bioC is induced with 1 mM IPTG at OD$_{600}$ of 0.4-0.6. The cultures are incubated at 30° C. with shaking at 180 rpm for 24-48 hours after induction before analysis.
Dicarboxylic Acid Production Analysis At multiple time points after inducing gene expression, 100 μL aliquots are taken from the culture, mixed with 100 μL of HPLC grade methanol, and filtered through a 0.5 mL 10 kDa amicon spin filter, and analyzed by liquid chromatography-mass spectrometry (LCMS). Dicarboxylic acids are quantified using a standard curve with authentic standards of C9, C11, C13, and C15 saturated dicarboxylic acids (Sigma Aldrich, TCI).
Results:
Comparing Dicarboxylic Acid Production in *E. coli* Using bcBioC Several strains are tested expressing 'tesA and bioC (*B. cereus*) and varied the expression strength of bioC in the presence and absence of genomic bioH. The titers of brassylic acid (C13 diacid) are indicated below:

ΔfadE E5C.bioC+B5K.'tesA: 17.3±0.3 μM
ΔfadE (DE3) E7C.bioC+B5K.'tesA: 3.0±0.1 μM
ΔfadEΔbioH (DE3) E5C.bioC+B5K.'tesA: 21.7±0.4 μM
ΔfadEΔbioH (DE3) E7C.bioC+B5K.'tesA: 14.7±0.4 μM
ΔfadEΔbioH (DE3) E5C.RFP+B5K.'tesA: ~0 μM The highest titer of brassylic acid is observed when bioC expression is driven by $P_{lacUV5}$, and when the bioH gene is removed. Approximately 0.1 μM C13 dicarboxylic acid methyl ester is also detected in these samples.

Diacid Production as a Function of Time Using pBioC and kBioC

Production of C13 and C15 dicarboxylic acids are measured in the following strains:

ΔfadEΔbioH E5C.pbioC+B5K.'tesA
ΔfadEΔbioH E5C.kbioC+B5K.'tesA

Figure 10A:
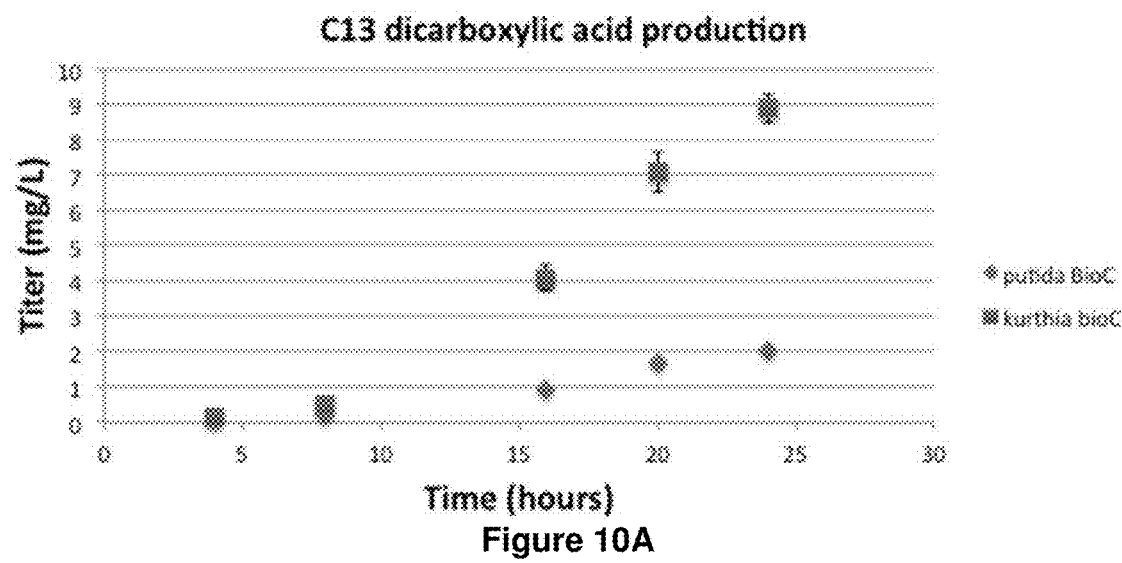
FIG. 10A. Production of C13 dicarboxylic acid as a function of time in the pBioC and kBioC production strains.
Figure 10B:
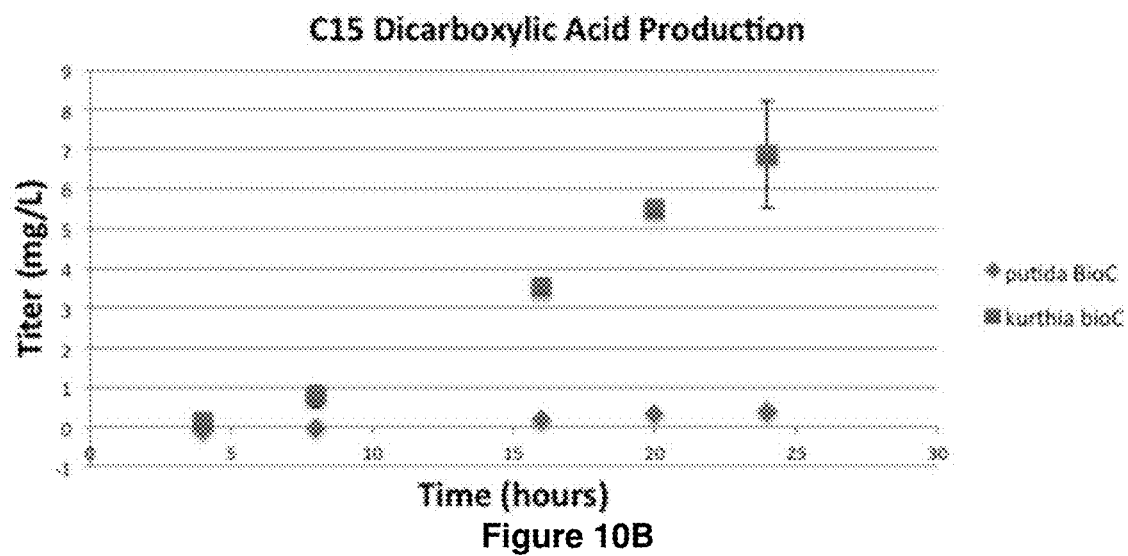
FIG. 10B. Production of C15 dicarboxylic acid as a function of time in the pBioC and kBioC production strains.

The results are shown in FIGS. 10A and 10B.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant genetically modified host cell comprising:
   (a) a S-adenosyl-methionine-dependent methyl transferase (BioC) that catalyzes a methyl transfer to an acyl-ACP species with a free carboxylate group distal to the thioester bond to form a first intermediate compound, (b) enzymes having enzymatic activities that elongates the first intermediate molecule to form a second intermediate compound, wherein the enzymes of step (b) are fatty acid synthase (FAS), and (c) a cytosolic thiosterase ('TesA) that catalyzes a release of the first or second intermediate molecule from the ACP through thioester hydrolysis to form an α,ω-dicarboxylic acids (DCAs) having the chemical formula:

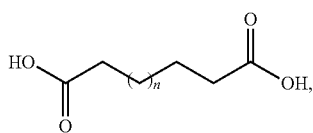
(II)

and/or a mono-methyl ester derivative of dicarboxylic acids (DCAMME) having the chemical formula:

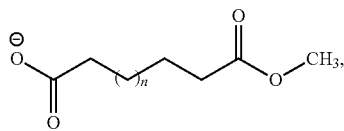
(I)

wherein n is an integer from 1 to 30;
wherein the recombinant genetically modified host cell is reduced or lacks a pimeloyl-acyl carrier protein methyl ester esterase (BioH) enzymatic activity, wherein if the unmodified host cell has a native BioH enzymatic activity then the native BioH has a reduced expression or is knocked-out.

2. The recombinant genetically modified host cell of claim 1, wherein the 'TesA catalyzes the release of the first or second intermediate molecule from the ACP through thioester hydrolysis to form the DCAMME having the chemical formula:

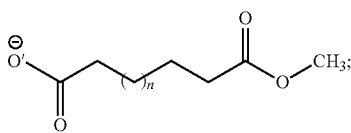
(I)

wherein n is an integer from 1 to 30.

3. The recombinant genetically modified host cell of claim 1, wherein the 'TesA catalyzes the release of the first or second intermediate molecule from the ACP through thioester hydrolysis to form the DCA having the chemical formula:

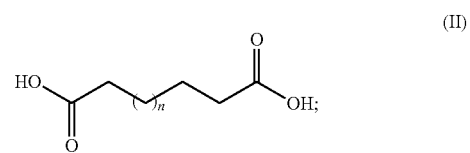
(II)

wherein n is an integer from 1 to 30.

4. The recombinant genetically modified host cell of claim 1, wherein the DCA comprises a main carbon chain with an odd number of carbon atoms.

5. The recombinant genetically modified host cell of claim 3, wherein the DCA is a C7 diacid, C9 diacid, C11 diacid, C13 diacid, C15 diacid, C17 diacid, C19 diacid, C21 diacid, C23 diacid, or C25 diacid.

6. The recombinant genetically modified host cell of claim 1, wherein the DCA is a C6 diacid, C8 diacid, C10 diacid, C12 diacid, C14 diacid, C16 diacid, C18 diacid, C20 diacid, C22 diacid, C24 diacid, or C26 diacid.

7. The recombinant genetically modified host cell of claim 1, wherein the host cell is a yeast cell or a bacterial cell.

8. The recombinant genetically modified host cell of claim 7, wherein the host cell is an *Escherichia* or *Bacillus* cell.

9. A method for producing dicarboxylic acids (DCAs) and mono-methyl ester derivatives of dicarboxylic acids (DCAMMEs) comprising:
   (a) providing the genetically modified host cell of claim 1,
   (b) culturing or growing the genetically modified host cell such that a DCA and/or a DCAMME is produced,
   (c) optionally separating the DCA and/or the DCAMME from the genetically modified host cell, and
   (d) optionally polymerizing the DCA and/or the DCAMME into a polyester or polyamide polymer.

10. The method of claim 9, wherein the polymerizing step comprises reacting the DCA with a diamine to produce a nylon.

11. The method of claim 10, wherein the diamine is an alkane diamine.

12. The method of claim 9, wherein the polymerizing step comprises reacting the DCA with a dialcohol to produce a polyester.

13. The method of claim 12, wherein the dialcohol is an alkane diol.

14. The method of claim 13, wherein the alkane diol is ethylene glycol, propane diol, or butanediol.

15. The method of claim 9, further comprises converting the DCA into a macrocyclic musk.

16. The method of claim 15, wherein the DCA is brassylic acid and the macrocyclic musk is ethylene brassylate.

* * * * *

SEQUENCE LISTING

<160> NUMBER OF SEQ ID NOS: 9

<210> SEQ ID NO 1
<211> LENGTH: 269
<212> TYPE: PRT
<213> ORGANISM: Bacillus cereus

<400> SEQUENCE: 1

Met Ile Asn Lys Thr Leu Leu Gln Lys Arg Phe Asn Val Ala Ala Val
1               5                   10                  15

Ser Tyr Asp Gln Tyr Ala Asn Val Gln Lys Lys Met Ala His Ser Leu
            20                  25                  30

Leu Ser Thr Leu Asn Arg Arg Tyr Ser Thr Asn Ser Ser Ile Arg Ile
        35                  40                  45

Leu Glu Leu Gly Cys Gly Thr Gly Tyr Val Thr Glu Gln Leu Ser Asn
    50                  55                  60

Leu Phe Pro Lys Ala Gln Ile Thr Ala Ile Asp Phe Ala Glu Ser Met
65                  70                  75                  80

Ile Ala Val Ala Lys Thr Arg Gln Asn Val Asn Asn Val Thr Phe Tyr
                85                  90                  95

Cys Glu Asp Ile Glu Arg Leu Arg Leu Glu Glu Thr Tyr Asp Val Ile
            100                 105                 110

Ile Ser Asn Ala Thr Phe Gln Trp Leu Asn Asp Leu Lys Gln Val Ile
        115                 120                 125

Thr Asn Leu Phe Arg His Leu Ser Ile Glu Gly Ile Leu Leu Phe Ser
    130                 135                 140

Thr Phe Gly Gln Glu Thr Phe Gln Glu Leu His Ala Ser Phe Gln Arg
145                 150                 155                 160

Ala Lys Glu Glu Lys Asn Ile Gln Asn Glu Thr Ser Ile Gly Gln Arg
                165                 170                 175

Phe Tyr Ser Lys Asn Gln Leu Arg His Ile Cys Glu Ile Glu Thr Gly
            180                 185                 190

Asp Val His Val Ser Glu Thr Cys Tyr Ile Glu Arg Phe Thr Glu Val
        195                 200                 205

Arg Glu Phe Leu His Ser Ile Arg Lys Val Gly Ala Thr Asn Ser Asn
    210                 215                 220

Glu Glu Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
            245                 250                 255

His Ala Leu Phe Val His Ile Thr Lys Glu Gly Lys Arg
            260                 265

<210> SEQ ID NO 2
<211> LENGTH: 251
<212> TYPE: PRT
<213> ORGANISM: Escherichia coli

<400> SEQUENCE: 2

Met Ala Thr Val Asn Lys Gln Ala Ile Ala Ala Phe Gly Arg Ala
1               5                   10                  15

Ala Ala His Tyr Glu Gln His Ala Asp Leu Gln Arg Gln Ser Ala Asp
                20                  25                  30

Ala Leu Leu Ala Met Leu Pro Gln Arg Lys Tyr Thr His Val Leu Asp
            35                  40                  45

Ala Gly Cys Gly Pro Gly Trp Met Ser Arg His Trp Arg Glu Arg His
        50                  55                  60

Ala Gln Val Thr Ala Leu Asp Leu Ser Pro Pro Met Leu Val Gln Ala
65                  70                  75                  80

Arg Gln Lys Asp Ala Ala Asp His Tyr Leu Ala Gly Asp Ile Glu Ser
                85                  90                  95

Leu Pro Leu Ala Thr Ala Thr Phe Asp Leu Ala Trp Ser Asn Leu Ala
            100                 105                 110

Val Gln Trp Cys Gly Asn Leu Ser Thr Ala Leu Arg Glu Leu Tyr Arg
        115                 120                 125

Val Val Arg Pro Lys Gly Val Val Ala Phe Thr Thr Leu Val Gln Gly
130                 135                 140

Ser Leu Pro Glu Leu His Gln Ala Trp Gln Ala Val Asp Glu Arg Pro
145                 150                 155                 160

His Ala Asn Arg Phe Leu Pro Pro Asp Glu Ile Glu Gln Ser Leu Asn
                165                 170                 175

Gly Val His Tyr Gln His His Ile Gln Pro Ile Thr Leu Trp Phe Asp
            180                 185                 190

Asp Ala Leu Ser Ala Met Arg Ser Leu Lys Gly Ile Gly Ala Thr His
        195                 200                 205

Leu His Glu Gly Arg Asp Pro Arg Ile Leu Thr Arg Ser Gln Leu Gln
    210                 215                 220

Arg Leu Gln Leu Ala Trp Pro Gln Gln Gln Gly Arg Tyr Pro Leu Thr
225                 230                 235                 240

Tyr His Leu Phe Leu Gly Val Ile Ala Arg Glu
                245                 250

<210> SEQ ID NO 3
<211> LENGTH: 276
<212> TYPE: PRT
<213> ORGANISM: Kurthia sp 538-KA26

<400> SEQUENCE: 3

Met Ile Asp Lys Gln Leu Leu Ser Lys Arg Phe Ser Glu His Ala Lys
1               5                   10                  15

Thr Tyr Asp Ala Tyr Ala Asn Val Gln Lys Asn Met Ala Lys Gln Leu
                20                  25                  30

Val Asp Leu Leu Pro Gln Lys Asn Ser Lys Gln Arg Ile Asn Ile Leu
            35                  40                  45

```
Glu Ile Gly Cys Gly Thr Gly Tyr Leu Thr Arg Leu Leu Val Asn Thr
 50                  55                  60

Phe Pro Asn Ala Ser Ile Thr Ala Val Asp Leu Ala Pro Gly Met Val
 65                  70                  75                  80

Glu Val Ala Lys Gly Ile Thr Met Glu Asp Arg Val Thr Phe Leu Cys
                 85                  90                  95

Ala Asp Ile Glu Glu Met Thr Leu Asn Glu Asn Tyr Asp Leu Ile Ile
            100                 105                 110

Ser Asn Ala Thr Phe Gln Trp Leu Asn Asn Leu Pro Gly Thr Ile Glu
            115                 120                 125

Gln Leu Phe Thr Arg Leu Thr Pro Glu Gly Asn Leu Ile Phe Ser Thr
130                 135                 140

Phe Gly Ile Lys Thr Phe Gln Glu Leu His Met Ser Tyr Glu His Ala
145                 150                 155                 160

Lys Glu Lys Leu Gln Leu Ser Ile Asp Ser Ser Pro Gly Gln Leu Phe
                165                 170                 175

Tyr Ala Leu Glu Glu Leu Ser Gln Ile Cys Glu Glu Ala Ile Pro Phe
            180                 185                 190

Ser Ser Ala Phe Pro Leu Glu Ile Thr Lys Ile Glu Lys Leu Glu Leu
            195                 200                 205

Glu Tyr Phe Gln Thr Val Arg Glu Phe Phe Thr Ser Ile Lys Lys Ile
210                 215                 220

Gly Ala Ala Asn Ser Asn Lys Glu Asn Tyr Cys Gln Arg Pro Ser Phe
225                 230                 235                 240

Phe Arg Glu Leu Ile Asn Ile Tyr Glu Thr Lys Tyr Gln Asp Glu Ser
                245                 250                 255

Gly Val Lys Ala Thr Tyr His Cys Leu Phe Phe Lys Ile Ile Lys His
            260                 265                 270

Ala Pro Leu Pro
            275

<210> SEQ ID NO 4
<211> LENGTH: 269
<212> TYPE: PRT
<213> ORGANISM: Clostridium thermocellum

<400> SEQUENCE: 4

Met Ile Asn Lys Thr Leu Leu Gln Lys Arg Phe Asn Val Ala Ala Val
  1               5                  10                  15

Ser Tyr Asp Gln Val Ala Asn Val Gln Lys Lys Met Ala His Ser Leu
                 20                  25                  30

Leu Ser Thr Leu Asp Arg Arg Tyr Ser Ala Asn Ser Ser Ile Arg Ile
             35                  40                  45

Leu Glu Leu Gly Cys Gly Thr Gly Tyr Val Thr Glu Gln Leu Ser Asn
 50                  55                  60

Leu Phe Pro Lys Ala His Ile Thr Ala Ile Asp Phe Ala Glu Ser Met
 65                  70                  75                  80

Ile Ala Val Ala Lys Thr Arg Gln Asn Val Lys Asn Val Met Phe Tyr
                 85                  90                  95

Cys Glu Asp Ile Glu Arg Leu Gln Leu Glu Glu Thr Tyr Asp Val Ile
            100                 105                 110

Ile Ser Asn Ala Thr Phe Gln Trp Leu Asn Asp Leu Lys Gln Val Ile
            115                 120                 125

Arg Asn Leu Phe His His Ser Leu Ile Asp Gly Ile Leu Leu Phe Ser
130                 135                 140
```

```
Thr Phe Gly Gln Glu Thr Phe Gln Glu Leu His Thr Ser Phe Gln Arg
145                 150                 155                 160

Ala Lys Glu Glu Lys Asn Ile Gln Asn Glu Thr Ser Ile Gly Gln Arg
                165                 170                 175

Phe Tyr Ser Lys Asn Gln Leu Arg His Ile Cys Glu Val Glu Thr Gly
            180                 185                 190

Asp Val His Val Ser Glu Thr Cys Tyr Ile Glu Arg Phe Thr Glu Val
            195                 200                 205

Arg Glu Phe Leu His Ser Ile Arg Lys Val Gly Ala Thr Asn Ser Asn
        210                 215                 220

Glu Glu Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
                245                 250                 255

His Ala Leu Phe Met His Ile Thr Lys Glu Gly Lys Arg
                260                 265

<210> SEQ ID NO 5
<211> LENGTH: 260
<212> TYPE: PRT
<213> ORGANISM: Chlorobium tepidum

<400> SEQUENCE: 5

Met Asn Gly Val Ile Asp Lys Gln Leu Val Arg Arg Phe Arg Arg
1               5                   10                  15

Ala Leu Pro Thr Tyr Ala Gly His Ala Glu Val Gln Arg Arg Met Ala
                20                  25                  30

Val Arg Leu Val Ala Leu Ile Glu Asn Ala Gly Ala Ser Thr His Leu
            35                  40                  45

Gly Arg Val Phe Glu Phe Gly Ser Gly Ser Ala Met Leu Thr Ser Ile
        50                  55                  60

Leu Phe Glu Arg Tyr Ser Ala Asn Glu Phe Phe Ala Asn Asp Leu Val
65                  70                  75                  80

Ala Glu Ser Arg Ala Phe Val Glu Lys Ala Val Thr Gly Arg Asn Val
                85                  90                  95

Glu Arg Leu Thr Phe Leu Pro Gly Asp Val Glu Arg Leu Asp Pro Leu
            100                 105                 110

Pro Gly Asn Leu Asp Leu Ala Val Ser Asn Ala Thr Val Gln Trp Leu
        115                 120                 125

His Asp Pro Ala Arg Phe Phe Asp Arg Leu Ala Thr Ser Val Lys Pro
    130                 135                 140

Gly Gly Ile Val Ala Phe Ser Thr Phe Gly Ala Glu Asn Met His Glu
145                 150                 155                 160

Ile Ala Ala Leu Gly Glu Ala Ala Leu Pro Tyr Arg Ser Leu Asp Lys
                165                 170                 175

Ile Ala Ala Leu Ser Gly Glu Leu Phe Glu Leu Val Ala Ile Glu Asp
            180                 185                 190

Asp Ile Val Arg Gln Glu Phe Asp Thr Pro Glu Ala Val Leu Arg His
        195                 200                 205

Ile Arg Lys Thr Gly Val Asn Gly Val Ala Arg Arg Ala Trp Thr Arg
    210                 215                 220

Ser Gln Tyr Leu Asp Phe Leu Gln Arg Tyr Arg Ser Ala Tyr Pro Ser
225                 230                 235                 240

Gly Glu Gly Val Thr Leu Thr Trp His Pro Val Tyr Cys Cys Phe Arg
```

```
                    245                 250                 255

Lys Lys Lys Ser
            260

<210> SEQ ID NO 6
<211> LENGTH: 255
<212> TYPE: PRT
<213> ORGANISM: Serratia marcescens

<400> SEQUENCE: 6

Met Thr Ser Ala Asn Asp Thr Val Asn Lys Gln Ala Val Ala Ser Ala
1               5                   10                  15

Phe Ser Arg Ala Ala Gly Ser Tyr Asp Ala Ala Ala Leu Gln Arg
            20                  25                  30

Asp Val Gly Glu Arg Leu Leu Gly Met Gly Ser Ser His Pro Gly Glu
            35                  40                  45

Gln Leu Leu Asp Ala Gly Cys Gly Thr Gly Tyr Phe Ser Arg Met Trp
        50                  55                  60

Arg Glu Arg Gly Lys Arg Val Thr Ala Leu Asp Leu Ala Pro Gly Met
65                  70                  75                  80

Leu Asp Val Ala Arg Gln Arg Gln Ala Ala His His Tyr Leu Leu Gly
                85                  90                  95

Asp Ile Glu Gln Val Pro Leu Pro Asp Ala Ala Met Asp Ile Cys Phe
            100                 105                 110

Ser Ser Leu Val Val Gln Trp Cys Ser Asp Leu Pro Ala Ala Leu Ala
        115                 120                 125

Glu Leu Tyr Arg Val Thr Arg Pro Gly Gly Val Ile Leu Phe Ser Thr
    130                 135                 140

Leu Ala Ala Gly Ser Leu Gln Glu Leu Gly Asp Ala Trp Gln Gln Val
145                 150                 155                 160

Asp Gly Glu Arg His Val Asn Ala Phe Leu Pro Leu Thr Gln Ile Arg
                165                 170                 175

Thr Ala Cys Ala Ala Tyr Arg His Glu Leu Val Thr Glu Leu Arg Thr
            180                 185                 190

Leu Asn Tyr Pro Asp Val Met Thr Leu Met Arg Ser Leu Lys Gly Ile
        195                 200                 205

Gly Ala Thr His Leu His Gln Gly Arg Glu Gly Gly Leu Met Ser Arg
    210                 215                 220

Gly Arg Leu Ala Ala Leu Gln Ala Ala Tyr Pro Cys Arg Gln Gly Gln
225                 230                 235                 240

Phe Pro Leu Ser Tyr His Leu Ala Tyr Gly Val Ile Tyr Arg Glu
                245                 250                 255

<210> SEQ ID NO 7
<211> LENGTH: 251
<212> TYPE: PRT
<213> ORGANISM: Erwinia herbicola

<400> SEQUENCE: 7

Met Ser Leu Val Asn Lys Arg Ala Val Ala Ala Phe Gly Arg Ala
1               5                   10                  15

Ala Gln Ser Tyr Asp Ser His Ala Gln Leu Gln Arg Gln Ser Ala Asp
            20                  25                  30

Leu Leu Leu Ala Lys Leu Gly Glu Arg Arg Pro Ala Ser Val Leu Asp
        35                  40                  45

Ala Gly Cys Gly Pro Gly Ser Met Ser Arg Tyr Trp Arg Asp Ala Gly
```

-continued

```
    50                  55                  60

Ala Glu Val Thr Ala Leu Asp Leu Ser Leu Pro Met Leu Arg Gln Ala
65                  70                  75                  80

Gln Ser Gln Gln Ala Ala Gln His Tyr Val Ala Ala Asp Ile Glu Ala
                85                  90                  95

Leu Pro Leu Ala Asp Ala Arg Phe Asp Leu Ala Trp Ser Asn Leu Ala
            100                 105                 110

Val Gln Trp Cys Asn Asp Leu Gly Gln Ala Leu Lys Ser Leu His Arg
        115                 120                 125

Val Val Arg Pro Gly Gly Ala Val Ala Phe Thr Thr Leu Ala Ser Gly
    130                 135                 140

Ser Leu Pro Glu Leu His Gln Ala Trp Gln Ala Val Asp Ser Arg Leu
145                 150                 155                 160

His Ala Asn Arg Phe Leu Ala Glu Glu Thr Leu Ala Glu Thr Val Ser
                165                 170                 175

Ala Trp Arg Gly Gln Trp Gly Ile Glu Pro Val Thr Leu Ala Phe Asp
            180                 185                 190

Asp Ala Leu Ala Ala Met Arg Ser Leu Lys Gly Ile Gly Ala Thr His
        195                 200                 205

Leu His Ala Gly Arg His Asn Thr Pro Leu Thr Arg Gly Gln Leu Gln
    210                 215                 220

Arg Leu Gln Leu Ala Trp Pro Gln Gln Gln Gly Arg Cys Leu Leu Thr
225                 230                 235                 240

Tyr Ser Leu Phe Trp Gly Val Ile Glu Arg Asp
                245                 250

<210> SEQ ID NO 8
<211> LENGTH: 269
<212> TYPE: PRT
<213> ORGANISM: Bacillus cereus

<400> SEQUENCE: 8

Met Ile Asn Lys Thr Leu Leu Gln Lys Arg Phe Asn Gly Ala Ala Val
1               5                   10                  15

Ser Tyr Asp Arg Tyr Ala Asn Val Gln Lys Lys Met Ala His Ser Leu
            20                  25                  30

Leu Ser Ile Leu Lys Glu Arg Tyr Ser Glu Thr Ala Ser Ile Arg Ile
        35                  40                  45

Leu Glu Leu Gly Cys Gly Thr Gly Tyr Val Thr Glu Gln Leu Ser Lys
    50                  55                  60

Leu Phe Pro Lys Ser His Ile Thr Ala Val Asp Phe Ala Glu Ser Met
65                  70                  75                  80

Ile Ala Ile Ala Gln Thr Arg Gln Asn Val Lys Asn Val Thr Phe His
                85                  90                  95

Cys Glu Asp Ile Glu Arg Leu Arg Leu Glu Glu Ser Tyr Asp Val Ile
            100                 105                 110

Ile Ser Asn Ala Thr Phe Gln Trp Leu Asn Asn Leu Gln Gln Val Leu
        115                 120                 125

Arg Asn Leu Phe Gln His Leu Ser Ile Asp Gly Ile Leu Leu Phe Ser
    130                 135                 140

Thr Phe Gly His Glu Thr Phe Gln Glu Leu His Ala Ser Phe Gln Arg
145                 150                 155                 160

Ala Lys Glu Glu Arg Asn Ile Lys Asn Glu Thr Ser Ile Gly Gln Arg
                165                 170                 175
```

```
Phe Tyr Ser Lys Asp Gln Leu Leu His Ile Cys Lys Ile Glu Thr Gly
            180                 185                 190

Asp Val His Val Ser Glu Thr Cys Tyr Ile Glu Ser Phe Thr Glu Val
            195                 200                 205

Lys Glu Phe Leu His Ser Ile Arg Lys Val Gly Ala Thr Asn Ser Asn
            210                 215                 220

Glu Gly Ser Tyr Cys Gln Ser Pro Ser Leu Phe Arg Ala Met Leu Arg
225                 230                 235                 240

Ile Tyr Glu Arg Asp Phe Thr Gly Asn Glu Gly Ile Met Ala Thr Tyr
                    245                 250                 255

His Ala Leu Phe Ile His Ile Thr Lys Glu Gly Lys Arg
            260                 265

<210> SEQ ID NO 9
<211> LENGTH: 272
<212> TYPE: PRT
<213> ORGANISM: Pseudomonas putida

<400> SEQUENCE: 9

Met Thr Asp Leu Ser Arg Pro Thr Leu Pro Gly Ala Leu Pro Asp Lys
1               5                   10                  15

Arg Gln Val Ala Ala Ser Phe Ser Arg Ala Ala Ser Tyr Asp Ser
            20                  25                  30

Val Ala Ala Leu Gln Arg Ala Val Gly Leu Ser Leu Leu Glu Gln Leu
            35                  40                  45

Pro Ala Gly Leu Gln Pro Ser His Trp Leu Asp Leu Gly Ser Gly Thr
        50                  55                  60

Gly His Phe Ser Arg Met Leu Ala Glu Arg Phe Ala Gln Ala Gly Gly
65                  70                  75                  80

Val Ala Val Asp Ile Ala Glu Gly Met Leu Leu His Ala Arg His Val
                85                  90                  95

Lys Gly Gly Ala Gln Tyr His Val Val Gly Asp Ala Glu Arg Leu Pro
            100                 105                 110

Leu Arg Asp Ala Ser Val Asp Leu Val Phe Ser Ser Leu Ala Val Gln
            115                 120                 125

Trp Cys Asp Gln Phe Ala Ser Val Leu Ala Glu Ala Gln Arg Val Leu
            130                 135                 140

Arg Pro Gly Gly Val Leu Ala Phe Ser Ser Leu Cys Val Gly Thr Leu
145                 150                 155                 160

Asp Glu Leu Arg Ala Ser Trp Gln Ala Val Asp Gly Leu Val His Val
                165                 170                 175

Asn Arg Phe Arg Arg Phe Glu Asp Tyr Gln Arg Leu Cys Ala Ala Ser
            180                 185                 190

Gly Phe Glu Gln Leu Glu Leu Glu Arg Cys Pro His Val Leu His Tyr
            195                 200                 205

Pro Asp Val Arg Ser Leu Thr His Glu Leu Lys Ala Leu Gly Ala His
            210                 215                 220

Asn Leu Asn Pro Gly Arg Pro Ser Gly Leu Thr Gly Arg Ala Arg Met
225                 230                 235                 240

Gln Gly Leu Leu Gln Ala Tyr Glu Ala Phe Arg Gln Pro Ala Gly Leu
                245                 250                 255

Pro Ala Thr Tyr Gln Val Val Tyr Gly Val Leu Arg Lys Pro Leu Ala
            260                 265                 270
```